United States Patent
Bauer

[11] Patent Number: 6,096,497
[45] Date of Patent: Aug. 1, 2000

[54] ELECTROSTATIC ENZYME BIOSENSOR

[75] Inventor: Alan Joseph Bauer, Jerusalem, Israel

[73] Assignee: Biosensor Systems Design, Inc., Cedarhurst, N.Y.

[21] Appl. No.: 09/110,686

[22] Filed: Jul. 7, 1998

[30] Foreign Application Priority Data

Jun. 15, 1998 [IS] Iceland ..................................... 124903

[51] Int. Cl.⁷ .............. C12Q 1/00; A01N 1/02; G01N 27/26; C25D 5/00
[52] U.S. Cl. ................. 435/4; 435/287.1; 435/289.1; 435/817; 435/283.1; 204/403; 204/164; 204/193; 205/81; 205/372; 422/82.01; 422/50; 257/40; 257/43
[58] Field of Search .......... 435/4, 283.1, 289.1, 435/817; 204/403, 164, 193; 205/81, 372; 422/82.01, 50; 257/40, 43

[56] References Cited

U.S. PATENT DOCUMENTS

| | | | |
|---|---|---|---|
| 5,156,810 | 10/1992 | Ribi | 422/82.01 |
| 5,264,103 | 11/1993 | Yoshioka et al. | 204/403 |
| 5,543,326 | 8/1996 | Heller et al. | 435/817 |
| 5,585,646 | 12/1996 | Kossovsky et al. | 257/43 |
| 5,783,056 | 7/1998 | Hampp et al. | 204/403 |

Primary Examiner—Louise N. Leary

[57] ABSTRACT

The device described herein is an enzyme-based biosensor for detecting and/or quantifying molecules of interest. The biosensor relies on the following properties shared by all enzymes: (1) that enzymes are highly specific molecules designed to bind with only one analyte type or one class of analyte molecules; (2) that enzymes contain charges; (3) that enzymes undergo significant spacial fluctuation during periods of interaction with substrates; and (4) that these spacial fluctuations cause the charged moieties on the enzyme to move and thus generate a measurable electrostatic potential (voltage) in both the enzyme and support layers. The instant device determines analyte presence/concentration through measurement of changes in voltage or current in a conducting or semiconducting support material as a result of changes in the position of immobilized charged enzyme molecules during their interaction with analyte. More particularly, the instant device immobilizes enzyme molecules sufficiently close to a conducting or semiconducting layer to insure that any alteration in the position of charged groups of the enzyme during interaction with analyte will cause the generation of a voltage in the base layer. When the enzymes encounter the targeted analyte the enzymes move, thus causing the enzyme charges to move. The movement of charges, in turn, changes the electrostatic field around the enzymes and results in a corresponding generation of a dipole (as measured in a generated voltage) in the conducting or semiconducting base layer. The presence and quantity of generated voltage is used to signal the presence and quantity of analyte.

36 Claims, 2 Drawing Sheets

ELECTROSTATIC ENZYME BIOSENSOR

BACKGROUND OF THE INVENTION

1. Field of the Invention

This invention pertains to a biosensor for detecting and/or quantifying analytes. More particularly, this invention pertains to a universal biosensor based on activity-dependent changes in enzyme electrostatic fields and the methods of their detection.

2. Description of Related Art

Biosensors are devices that can detect and/or quantify analytes using known interactions between a targeted analyte and a biological macromoleculer binding agent such as an enzyme, receptor, DNA or antibody. Biosensors are unique in that they have applications in virtually all areas of human endeavor. In example, biosensors have utility in fields as diverse as blood glucose monitoring for diabetics, the recognition of poisonous gas and/or explosives, the detection of chemicals commonly associated with spoiled or contaminated food, genetic screening, and environmental testing.

Biosensors are commonly categorized according to two features, namely, the type of macromolecule utilized in the device and the means for detecting the moment contact occurs between the binding agent and the targeted analyte. Major classes of biosensors include enzyme (or catalytic) biosensors, immunosensors and DNA biosensors.

Enzyme (or catalytic) biosensors utilize one or more enzymes as the macromolecule and take advantage of the complimentary shape of the selected enzyme and the targeted analyte. Enzymes are proteins that perform most of the catalytic work in biological systems and are known for highly specific catalysis. The shape and reactivity of a given enzyme limit its catalytic activity to a very small number of possible substrates. Enzymes are also known for speed, working at rates as high as 10,000 conversions per second per enzyme molecule. Enzyme biosensors rely on the specific chemical changes related to the enzyme/analyte interaction as the means for recognizing contact with the targeted analyte. For example, upon interaction with an analyte, a biosensor may generate electrons, a colored chromophore or a change in pH as the result of the relevant enzymatic reaction. Alternatively, upon interaction with an analyte, an enzyme may cause a change in a fluorescent or chemiluminescent signal that can be recorded by an appropriate detection system.

Immunosensors utilize binding agents called antibodies. Antibodies are protein molecules that generally do not perform catalytic reactions but are designed to bind with specific foreign molecules, called antigens, that are at times associated with some disease states. Antibodies attach to antigens and either remove the antigens from the host and/or trigger an immune response. Antibodies are quite specific in their interactions and, unlike enzymes, they are capable of recognizing and selectively binding to very large bodies such as single cells. Thus, antibody-based biosensors allow for the identification of certain pathogens such as dangerous bacterial strains.

DNA biosensors utilize the complimentary nature of the DNA or RNA double-strands and are designed for the detection of DNA or RNA fragments usually associated with a given medical condition. A sensor generally uses a single-strand from a DNA double helix as the binding agent. The nucleic acid material in a given test sample is then denatured and placed into contact with the binding agent. If the strands in the test sample are complementary to the strands used as the binding agent, the two interact. The interaction can be monitored by various means such as a change in mass at the sensor surface or the presence of a fluorescent or radioactive signal. Alternative arrangements have binding of the sample of interest to the sensor and subsequent treatment with labeled probes to allow for identification of the sequence(s) of interest.

While the potential utility for biosensors is great and while hundreds of biosensors have been described in patents and in the literature, actual commercial use of biosensors remains limited. All enzyme biosensor designs set forth in the prior art contain one or more inherent weaknesses. Some lack the sensitivity and/or speed of detection necessary to accomplish certain tasks. Other such biosensors lack long-term stability. Still other biosensors cannot be sufficiently minaturized to be commercially viable or are prohibitively expensive to produce. Often biosensors must be pre-treated with salts and/or enzyme cofactors, a practice that is inefficient and bothersome. To date, virtually all enzyme biosensors are limited by the chemistries they employ to monitor contact between the sensing enzyme and the targeted analytes, regardless of whether the chemistry causes a pH change (generation of protons), a color change (generation or removal or a colored chromophore) or a change in oxidation state. One system takes advantage of a fluorescence change that occurs when glucose binds to a fluorescently-tagged glucose-binding protein. This system is hampered in its requirement for structural data and site-directed mutagenesis for the proper placement of the fluorescent probe.

The following references represent the closest prior art to the instantly claimed invention known to applicant as of the filing date of the instant application. We note that the binding of enzymes to solid supports is not new art; publications on the subject can be found in books and articles for well over two decades. Methods for enzyme immobilization for use in biosensor device construction have also been frequently reported in the literature and patents. The novel aspect of the instant invention is the chemistry-independent nature of the detection of enzyme action and thus substrate (analyte) presence:

(1) U.S. Pat. No. 5,156,810 to Ribi and U.S. Pat. No. 5,491,097 to Ribi et al. (hereinafter referenced as "the Ribi patents"). The Ribi patents teach biosensors employing a thin crystalline diyne surfactant polymeric electrically conducting layer. Specific binding pairs may be bound to the layer. Binding of an analyte or a reagent to the specific binding pair member layer may change the electrical, optical or structural properties of the layer for measurement of the analyte. The change in the polymeric layer provides for a measurement.

Contrary to the instant invention, the Ribi patents do not detect analytes by monitoring changes in voltages arising from deviations in the electrostic field surrounding an enzyme as it moves during contact with its substrate(s). In fact, the Ribi patents do not even indicate a preference for using an enzyme as the binding pair member. In the Ribi patents, the diyne binding layer is the critical detection component, while in the instant invention detection occurs away from the enzyme and its chemical supports. Any change in electrical property and/or conductivity referenced in the Ribi patents is due to charges that are released during specific chemical interactions between a binding pair rather than voltage or electromagentic radiation changes due to enzyme movements in response to the presence of the molecule of interest.

(2) *Immobilization of Protein Molecules onto Homogeneous and Mixed Carboxylate-Terminated Self-Assembled Monolayers* by Patel et al., *Langmuir* 1997, 6485–6490 (hereinafter referenced as "Patel"). Patel teaches binding of the protein catalase to gold surfaces modified by self-assembled monolayers (SAMs). Patel also teaches that the attachment of biomolecules, in particular proteins, onto solid supports is fundamental in the development of advanced biosensors. However, Patel does not teach an enzyme biosensor that measures contact with a targeted analyte by monitoring changes in voltage arising from deviations in the electrostatic field around enzymes as they move during contact with an analyte. In fact, Patel does not teach a functional biosensor of any sort, although as in all biosensors, detection of enzyme function depends on the chemistry performed by the bound enzyme, in this case, catylase.

(3) Wilner and his co-workers (*Assembly of Functionalized Monolayers of Redox Proteins on Electrode Surfaces: Novel Bioelectronic and Optobioelectronic Systems, Biosensors & Bioelectronics* 1997, 337–356; *NAD$^+$-Dependent Enzyme Electrodes: Electrical Contact of Cofactor- Dependent Enzymes and Electrodes, J. Am. Chem. Soc.*, 1997, 9114–9119) have used SAM's to anchor enzymes to gold electrodes. Yet, their biosensors rely on electron transfer from the sensing enzyme directly or through the SAM intermediate to the gold electrode. All sensors that employ an enzyme "oxidase" (an enzyme that performs chemistry that involves electron generation and/or transfer) alone or in tandem with other enzyme species will rely on oxidation-reduction chemistries by the oxidase to detect the molecule (glucose or lactose, for exmple) of interest (for examples, Yoshioka, et al. U.S. Pat. No. 5,651,869; Fennouh, et al., *Increased Paraoxon Detection with Solvents Using Acetylcholinesterase Inactivation Measured with a Choline Oxidase Biosensor, Biosensors & Bioelectronics,* 1997, 97–104). The vast majority of U.S. patents issued during the past few years for enzyme biosensors are for designs that employ "ampometric" detection of analyte via transfer of electrons from enzyme to electrode.

(4) Other enzyme biosensor devices that do not rely on electron transfer from enzyme active site to electrode still depend entirely on chemical means for determining the presence of analyte. Color (Gardiol, et al. *Development of a Gas-Phase Oxygen Biosensor Using a Blue Copper-Containing Oxidase, Enzyme Microb. Technol.* 1996, 347–352) or fluourescence changes (Tolosa, et al. *Optical Assay for Glucose Based on Luminescence Decay Time of the Long Wavelength Dye Cy5($T_M$) Sensors & Actuators B—Chemical,* 1997, 93–99) and pH changes (Blackburn, et al. *Potentiometric Biosensor Employing Catalytic Antibodies as the Molecular Recognition Element, Anal. Chem.* 1990, 2211–2216) are routinely used as the methods of detection in catalytic biosensor systems. Such requirements for observable chemistries significantly reduce the number of enzymes (and thus analytes) that can be employed in the currently available enzyme biosensor systems. The instant invention does not specifically monitor the enzyme reaction chemistries; rather, the voltage generated by the physical motion of the charged enzyme molecules during interaction with substrate(s) signals that the molecule of interest is present and at what concentration. While one U.S. patent does claim biological sensing as a function of molecular motion (U.S. Pat. No. 5,620,854 to Holzrichter and Siekhaus), this invention requires the use of a scanning probe microscope for determination of macromolecule action. The instant invention requires no such device and relies on the measurement of generated voltage or current.

The biosensor design described in this application is versatile, simple to use, inexpensive to produce, and demonstrates the long-term stability necessary for commercial application. Because the biosensor uses enzymes as the recognition agent, it is able to detect targeted analytes at a speed sufficient for any use. The motion of highly-charged enzyme molecules (as first described by Radmacher, et al. *Direct Observation of Enzyme Activity with the Atomic Force Microscope, Science,* 1994, 1577–1579) during contact with analyte instantly registers the presence of analyte. Since sensing depends on physical properties shared by all enzymes—and not on any particular enzyme/analyte chemistries—enzymes that perform reactions such as hydrolyses and isomerizations (and thus cannot be detected directly by the current chemistry-dependent biosensing systems) can now be utilized. This change in detection methodology opens the door to the sensing of thousands of new analytes. The biosensor has excellent sensitivity in detection and, in short, has all the properties and production features necessary for use in numerous domestic, military, law-enforcement, medical, and industrial applications.

SUMMARY OF THE INVENTION

The novel biosensor design disclosed herein is based on the fact that enzymes are highly charged species that move in a specific manner when the relevant substrate molecules are present. The biosensor utilizes a novel method of detecting an analyte wherein one or more enzyme molecules are first immobilized to a conducting or semiconducting support; this support is then monitored (by a voltmeter for example) for fluctuations in voltage or current as free electrons move relative to the changing enzyme electrostatic field specifically during periods of enzyme interaction with analyte. A measured voltage or current is indicative of enzyme motion during interaction with an analyte. A typical biosensor comprises: (i) a multilayer substrate comprising a conducting or semiconducting layer and an optional self-assembled monolayer (or other chemical entity that binds or coordinates enzymes to the conducting or semiconducting base support); (ii) enzyme molecules; and (iii) a means of measuring changes in voltage (or current) in the conducting or semiconducting layer in response to the enzyme motion.

DESCRIPTION OF THE PREFERRED EMBODIMENTS

Figure 1:
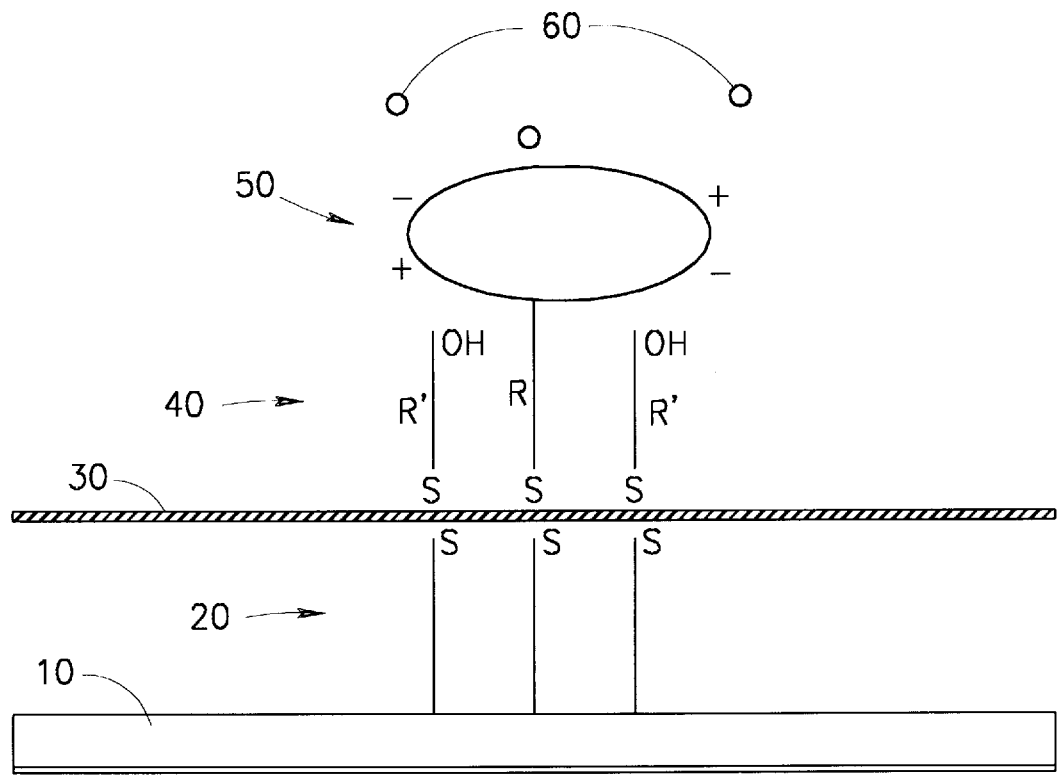
FIG. 1 illustrates a sample biosensor constructed on a non-conducting base material according to the instant invention. Other potential embodiments are not shown as they are similar to that represented in FIG. I.

The new biosensor design is based on the fact that enzymes are highly charged species that move during contact with their biological substrates. Enzymes, being a sub-class of proteins, are made up of amino acid building blocks and many of these building blocks are positively or negatively charged in solution. When an enzyme encounters an analyte on which it performs its catalytic chemistry, the enzyme undergoes nanometer-scale spatial fluctuations that alter the electrostatic field surrounding the enzyme. The biosensor described herein is designed to take advantage of the displacement of the charged residues of the enzyme molecules as the methodology of detection. This method is entirely new in the art. The critical steps of this method are first immobilizing one or more enzyme molecules on a solid support and then measuring the voltage or current produced in the support by the enzymes as a function of their physical motion in the presence of analyte. A change in the electrostatic field surrounding the enzyme (as measured by said generated of voltage or current) signals enzyme movement in response to interaction with analyte. The degree of electrostatic field changes can be correlated to the concentration of analyte.

A biosensor developed to use this new mode of detection comprises:

(i) a multilayer substrate comprising a conducting or semiconducting layer and an optional self-assembled monolayer (or other chemical entity) directly or indirectly bound to the conducting or semiconducting layer;

(ii) enzyme molecules bound to the conducting or semiconducting layer of the multilayer substrate optionally through direct or indirect binding with the self-assembled monolayer or other the "chemical entity" listed above; and (iii) a means for measuring a voltage or current generated by the function sensor.

The conductive layer may be any conducting or semiconducting substance in any form. Examples of suitable forms include foils, wires, wafers, chips, semiconductor devices and coatings deposited by any known deposition process. Gold, silver, and copper conductive layers chemisorb thiol, sulfide or disulfide funtional compounds, while other conductive layers may chemisorb these or other SAM-forming compounds (that include oxygen-containing compounds for etched silicon [SiH] and silicon-derivative compounds [trichiorosilanes, trimethoxysilanes, for example] for metal oxides). Preferred base layer materials include silicon, gold, silver, copper, aluminum, platinum, iridium palladium, rhodium, mercury, osmium, ruthenium, gallium arsenide, indium phosphide, mercury cadmium telluride, and the like. Aluminum foil, doped silicon wafers, and silver and gold coatings are particularly preferred. Silver and gold bind tightly to thiols, sulfides, and disulfides, while silicon (SiH surface) binds alcohols and carboxylic acids or ($SiO_2$ surface) silicon-based compounds such as trichlorosilanes.

The "self-assembled monolayer" (SAM) is a term of art and is herein defined as a type of molecule that can bind or interact spontaneously or otherwise with a metal, metal oxide, glass, quartz or modified polymer surface in order to form a chemisorbed monolayer. As the phrase "self-assembled" implies, a self-assembled monolayer is formed from molecules that bond with the surface upon their direct contact from solvent, vapor, or spray. As the word "monolayer" implies, a self-assembled monolayer possesses a molecular thickness, i.e., it is ideally no thicker than the length of the longest molecule used therein. Each of the molecules making up a self-assembled monolayer in this device includes a functional group that adheres to the base support and may include a pendant moiety that can interact with an enzyme molecule to be anchored above the monolayer. The device may also be constructed without the use of SAM's (i.e., by direct physical absorption of the enzyme molecules to the conducting or semiconducting layer).

A class of suitable SAM's for use in the instant invention has a functional group that forms a thiolate linkage when it comes into contact with the conductive layer (silver or gold); for etched silicon, alcohols bind through the hydroxyl moeity to the silicon surface. Appropriate SAM's include a wealth of sulfur containing compounds and organic alcohols. Notable among the former are organic thiols, sulfides, and disulfides.

Organic thiols corresponding to the general formula RSH where R represents an organic moeity. R can be aryl, alkyl, a combination of the two, long- or short-chain. Preferably the pendant functional group is chosen from those functional groups that are reactive with the amino ($-NH_2$) or other reactive groups on proteins, or that can be adapted to be reactive with said groups, or that provide stability to enzymes by serving as either a source of hydrophilic or hydrophobic stabilization. Functional groups that are reactive with amino groups or that are easily adapted to be reactive with amino groups include carboxylic acids that can be converted to more reactive functionalities. Functional groups that stabilize enzymes by providing a source of hydration include hydroxyl and carboxylic acid moeities. Hydrophobic stabilization can be provided by pendant methyl or other appropriate alkyl and aryl groups.

Organic sulfides correspond to the general formula RSR' where R and R' represent organic groups. The nature of R and R' can be varied to balance insulation and electrical connectivity between the enzymes and the conductive layer. Once again, the terminal functional groups are chosen from those functional groups that are reactive with the amino ($-NH_2$) or other functional groups on enzymes, or that can be easily adapted to be reactive with said groups, or that provide stability to enzymes by serving as a source of hydrophilic or hydrophobic stabilization.

Organic disulfides correspond to the general formula RS—SR' where R and R' have the meanings given above.

Preferably the SAM system employs two chemicals (a "mixed SAM"), one that provides for a hydrophilic layer under the enzyme and is directly and chemically bound to the conductive layer (FIG. 1). A hydrophilic layer beneath the enzyme molecules provides pseudo-hydration for the enzyme molecules and contributes to their long-term stability—even under anhydrous storage conditions.

Preferably the pendant group of the second chemical of the mixed SAM's is reactive with enzyme amino groups (or other protein functionalities) or is easily modified to become reactive with amino groups (or other protein functionalities). This compound serves to bind enzymes to the conductive layer through the SAM. Both compounds have a thiol group for gold and silver supports, trichloro or trimethoxy (triethoxy) silane group for metal oxides and hydroxyl or carboxylic acid functionality for SiH, while the pendant group in all cases is selected so as to either stabilize bound enzyme molecules or to allow for binding of the the enzyme moleucles to the surface.

The most preferred SAM for gold and silver supports is formed from a combination of mercapto acid (for enzyme binding), such as 11-mercaptoundecanoic acid (11-MUA), and a thiol alcohol having the formula HS—R"—OH where the R" represents an organic group. The nature of R" can be varied to balance insulation and electrical connectivity between the enzyme and the conductive layer. Thus, if one wishes to have a less sensitive device, he/she can select a SAM system appropriate for greater damping of the signal generated by the moving enzymes. Exemplary R" groups are the phenyl group (benze ring) or the alkyl moeity, $(CH_2)_6$. The ratio of these compounds can be altered to allow for more or less enzyme binding to the sensor surface. The preferred ratio is 1:10 (mercapto acid:HS—R"—OH).

If 11-MUA is used, it is preferably further modified with 1-ethyl-3-[3(dimethylamino)propyl] carbodiimide hydrochloride (known alternatively as EDAC or EDC) and N-hydroxysuccinimide (NHS). These compounds modify 11-MUA to make it even more reactive to enzyme amino groups.

It is to be understood that the foregoing list of SAM materials is merely representative and not all-inclusive. A SAM may not even be required in certain applications such as disposable detectors (where a simple "yes/no" response is necessary). Protein molecules themselves are insulating and thus the directly absorbed enzyme molecules can act to insulate the support from the changing electric fields. Many compounds other than those listed above can be used to form the SAM layer in the instant invention. Virtually all enzyme immobilization strategies are appropriate for the instant invention.

The enzyme component is neither limited in type or number. Naturally-occuring, mutated, chemically synthesized or modified enzymes may be used in this device. In this sense, the biosensor is "universal." The biosensor can employ any enzyme because it relies on the following properties shared by all enzymes:

(1) that enzymes are highly specific molecules designed to bind only with one analyte type or one class of analyte molecules;

(2) that enzymes have associated electrostatic fields due to charges on amino acid side chains, the charged enzyme termini and fixed molecular dipoles;

(3) that enzymes undergo significant spatial fluctuations (in all directions) specifically during periods of interaction with substrate(s); and (4) that these spatial fluctuations cause the charges and dipoles of the enzymes to change their physical location and, thereby, alter the electrostatic profile of the enzymes and thus generate an electrostatic potential (voltage) in the support material.

The universal nature of the biosensor is preserved during binding of enzyme to the conductive support because the binding means utilizes the fact that all enzymes contain amino groups or can be physically absorbed ("physisorbed") to a support surface. Finally, the voltage (or current) generation which signals contact with an analyte does not rely on any specific enzyme/analyte chemistry. This feature distinguishes the instant invention with all known enzyme biosensors.

The enzymes preferably rest within a distance not much greater than 3 nanometers (closest approach) from the conducting or semiconducting layer so as to allow for easy measurement of the voltage (current) produced by moving enzyme.

The biosensor further contains a means for detecting changes in the electrostatic field surrounding the enzymes. The measurement entails detection of the voltage or current generated in the conducting or semiconducting layer during enzyme interaction with analyte.

In example, the enzyme movement during interaction with analyte will typically alter the vertical position of the enzyme relative to the support. Additionally, there are lateral motions of the enzyme molecules, and they will cause electrons to move in the nearby conducting or semiconducting support layer. The enzyme charges act like electrons in a wire that can cause—through generated B- and E-fields—electrons to flow in an adjacent conducting wire (separated by an insulating region). The voltage (or current) can be measured in the conducting or semiconducting layer in response to the motions of the charged enzyme; these motions occur when analyte is present. An electrode is herewith defined as a wire, electrical lead or the like that is connected at one end to a voltage or current meter (or the like), and at the other end to the enzyme/support unit. The specific design of the electronics unit will be the subject of a separate patent filings for each unique sensor design. There are an unlimited number of arrangements of the two electrodes on the sensor to allow for the measurement of the voltage (current) produced by the functioning sensor. The easiest measurement takes advantage of the lateral motions of the enzymes during contact with analyte. As the enzymes move, electrons in the support move, and net voltage differences occur between different points on the support material. The insulating material (oxide, SAM layer or even the protein itself) between enzyme and support is critical in allowing for electron motion in the base layer in response to the enzyme fluctuations. For a typical experiment, the electrodes are attached to the same or opposite sides of the sensor (in a region not in contact with solution). Electron flux in the conducting or semiconducting support is recorded as a generated voltage (current), and the specific voltage (current) values are correlated to analyte concentrations. See Example 10 and FIG. 2 below.

There are several points to note in regards to the novel method of detection of enzyme motion. Normally, a conducting material is at a single potential (voltage) at all points along its surface. In the instant invention, enzymes are in continual and rapid motion; the result is a changing flux of electrons in the conducting or semiconducting material in response to the motion of approximately $10^{12}$ enzyme molecules per $cm^2$ of support material. The implications are signficant. Firstly, sensing can take place far away from the point of enzyme-analyte contact, as the effects of electron motion are propagated throughout the base material (for a conductor). Detection can even be performed on the side opposite to that in direct contact with the analyte. This fact allows for "food sensing" or the sensing of samples in closed systems. One side (with enzyme bound) of the sensor contacts the material of interest, while the electrodes (or a voltage-sensitive compound) used in measurement are contacted to two points on the reverse side. This is an important feature of this electrostatic enzyme biosensor. Experience of the inventor has shown that the enzyme motion generates a rapidly changing electrostatic potential in the enzyme layer; this flux in potential is reflected in rapidly changing voltages as measured across a conducting metal support. Voltages typically range between 0 and 300 millivolts during a bacteria sensing experiment with the enzyme lysozyme. Though the voltage readings fluctuate, the range of values is closely associated with the concentration of bacteria (analyte) present in the sample. Enzyme monolayers, SAM's and native oxide layers do not interfere with the direct electrical contacting of the electrodes to the conducting or semiconducting material (observation of inventor).

The biosensor described in this application is very versatile in its preparation. A simple food sensor may have the enzyme lysozyme physically absorbed to a piece of aluminum foil. A more complex medical sensor may require the use of a solid-state electronic device or the deposition of a metal on a chemically unreactive surface. An example of the latter embodiment of the instant invention is herewith described.

A preferable biosensor for non-conducting support materials (FIG. 1) contains a multilayer substrate comprising the following layers:

(a) a non-conducting base layer;

(b) an optional intermediate self-assembled monolayer positioned above the base layer;

(c) an intermediate conductive layer positioned above the base layer and, if present, above the intermediate self-assembled monolayer; and (d) an optional outer self-assembled monolayer positioned above the intermediate conductive layer comprising one or more compounds that chemically bind with enzymes and/or provide physcial/chemical stabilization to the chemically bound enzymes.

The conductive layer and outer self-assembled monolayer are as previously described.

The base layer provides structural support. Any base layer may be used but the preferred base layers naturally contain, or are modified to contain, chemically bound silicon dioxide groups. Preferred base layers are made of glass, quartz, silicon and modified organic polymers such as the reaction product of an oxidized polymer with silicon tetrachloride and water. The most preferred base layer in this specific case is the reaction product of polyethylene with silicon tetrachloride and water.

The optional intermediate SAM provides a strong adhesive bond between the base layer and the conductive layer. Other means of attachment can be employed, such as the use of a transition metal. However, these other means have disadvantages, most notably inferior adhesion and, in the case of transition metals, diffusion of metal atoms (which affects the electronic properties of the conductive layer). Therefore, the use of an intermediate SAM between the base layer and the conductive layer is preferred.

The intermediate SAM is preferably formed from a compound that contains both a silicon group and a sulfide or thiol group. The silicon group enables the SAM to bind to silicon dioxide groups in the preferred base layer and the sulfide or thiol group enables the SAM to bind to the conductive layer. The most preferred intermediate SAM is formed from a compound having the formula $(CH_3O)_y$—Si—$(CH_2)_z$—SH wherein y and z, independently, may be zero or any integer. Preferably both y and z are 3.

A biosensor according to a preferred embodiment is illustrated in FIG. 1. FIG. 1 shows a silicon dioxide functional base layer (10). A first SAM (20) is formed on one side of the base layer (10) and is connected to the base layer (10) by direct chemical siloxane linkages. A silver or gold layer (30) is formed on top of the first SAM layer (20) and connected to the first SAM layer (20) by direct chemical sulfur linkages. A second SAM layer (40) is formed on top of the silver layer (30) and is connected to the silver layer (30) by direct chemical sulfur linkages to the deposited metal. Two molecules make up the second SAM layer (40)—a first molecule that is terminated with alcohol groups and a second molecule that is terminated with a group that is reactive with enzyme amino groups (or can be made reactive with said functional groups). Enzymes (50) are attached to the second SAM (40) by reacting amino functionalities on the enzymes (50) with reactive groups on the second SAM (40). The enzymes (50) contain various positive and negative charges from the amino acid residues that make up the enzyme sequence (50). Analyte molecules (60) come in contact with enzyme molecules (50). A voltage is generated in the silver layer by the physical displacement of charged groups on the enzyme molecules as a result of enzyme motions in the presence of the specific molecule of interest (analyte).

Figure 2A:
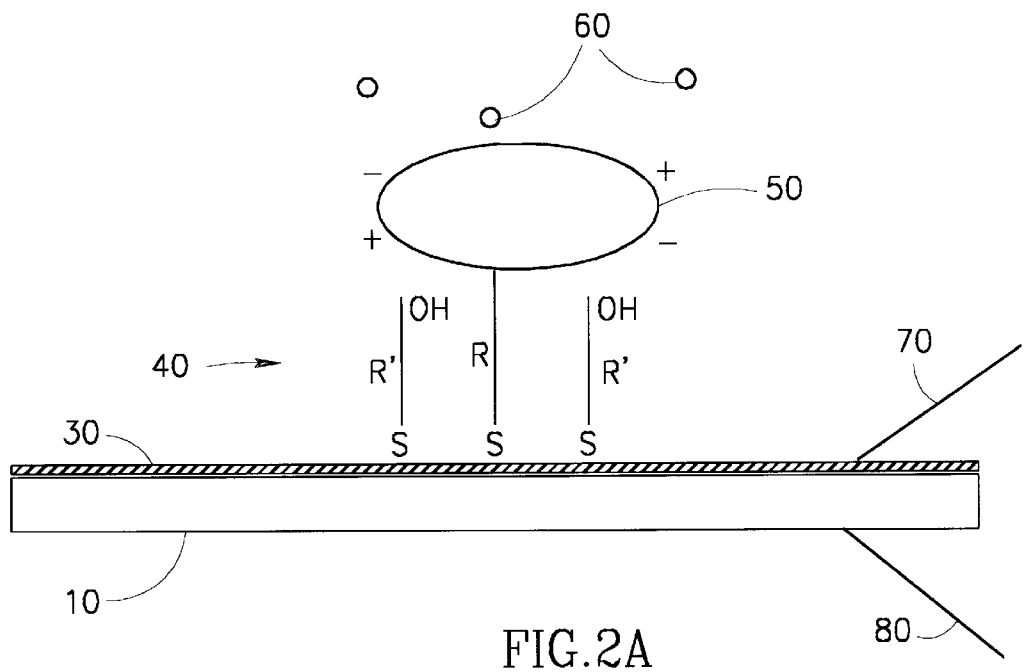
FIG. 2 illustrates potential positions for the electrodes during the measurement of voltage generated by a functioning sensor.
Figure 2B:
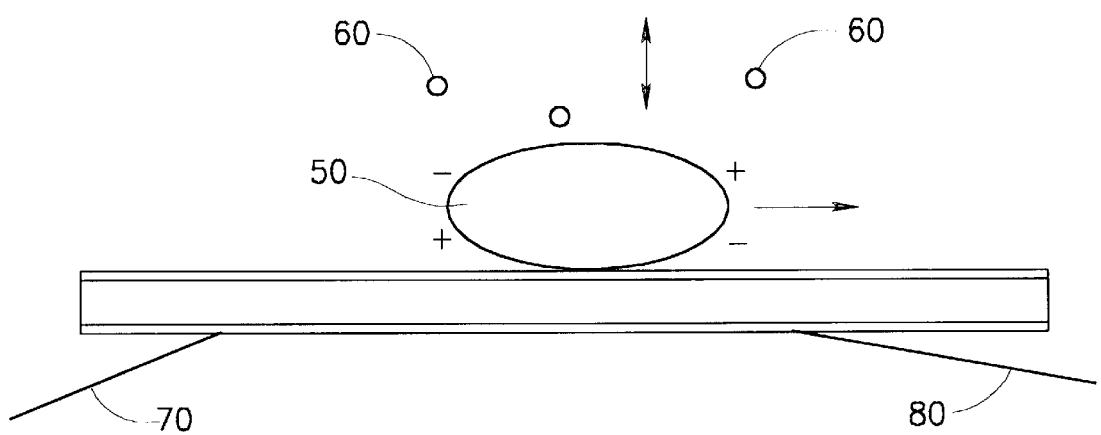

In FIG. 2, the electrodes are shown in two possible configurations. In both cases, the electrodes are placed on dry portions of the sensor at some distance from the site of enzyme-analyte interaction. Electrode 1 (70) is placed directly on the conducting or semiconducting material (either side). Electrode 2 (80) can be placed either on the same side of the conducting material (but obviously not touching electrode one) or on the opposite side. As the measurements involve determination of the voltage (or current) flux in the conducting or semiconducting material in response to total enzyme motions (in the presence of analyte), specific location of electrodes is not critical (other than they must be kept dry to avoid spurious voltages) but should be standardized for a given sensor type. In all cases, the electrodes connect the functional sensor to some type of voltage/current measurement device or voltage/current sensitive compound. As described previously, the instant invention allows one to measure the voltage fluctuation on the "outside" of a sensor while the "inside" of the sensor is in contact with a solution, such as milk in a bag or carton. This "dry" sensing is a major advantage of the instant invention detection methodology.

The instant invention has several advantages.

First, the invention allows for the creation of very small biosensors due to the ability to attach enzymes in high concentration. The device, independent of electrical connections, can be made as small sub-millimeter dimensions (appropriate for IC fabrication).

Second the biosensor is inexpensive and quick to assemble. A fully functional biosensor can be made in well under 24 hours. A bacteria sensor appropriate for food sensing and "bio-threat" detection can be prepared in thirty minutes from physisorbed hen egg-white lysozyme (whose substrate is the sugar portion of a bacteria cell wall) on standard aluminum foil. Cost per sensor is well under one cent per sensor.

Third, the biosensor exhibits high detection sensitivity. As stated, enzymes can interact with as many as 10,000 analyte molecules per second per enzyme molecule. This high turnover rate, in combination with the high density (estimated as approximately $10^{12}$ enzyme molecules per $cm^2$ of support material) of enzymes that can be placed on the surface of the biosensor, results in a highly-sensitive device.

Fourth, the biosensor exhibits long-term stability. In part, this is due to the simplicity of the design that significantly reduces the number of materials required. Primarily this is due to the stability of the materials and the SAM's optionally used to make the device. Bound enzymes are known for their ruggedness, especially when compared to enzymes that are free in solution. The hydroxyl-terminated SAM provides hydrophilic stabilization to the immobilized enzyme, while a naturally-occurring water monolayer above the enzymes and the enzyme—enzyme interactions on the device will further add to the stability of the device even under "anhydrous" storage conditions. The bacteria sensor described previously is stored dry and shows response within seconds when contacted to bacteria-containing solutions.

Fifth, the biosensor provides an instantaneous readout. This is a major benefit as most systems have time-delays due to detection response. This feature is absolutely critical in such applications as poison gas detection or routine food monitoring. Enzyme action is instantaneous with the arrival of analyte, and the measured response follows immediately.

Sixth, the design is highly flexible. For instance, if one wishes to detect several molecules at once, several such devices can be grouped together (a benefit of small size) in a "biochip format". In addition, if one wishes to adjust the sensitivity of the device a number of means are available. In example, one can change the number, type or chemical composition of the enzyme component through chemical or genetic manipulations. Alternatively, the length or nature of the organic groups in the SAM layer can be altered. In addition, the conducting or semiconducting layer can be chosen from a variety of materials all having different electronic properties. Finally, the orientation of the enzymes on the device can be manipulated (currently the enzymes are attached in a non-oriented fashion so that enzyme samples can be used directly as received).

Seventh, the biosensor is simple to use. One simply places the sample of interest in contact with the biosensor and the device electronics or voltage-sensitive dye determines target analyte presence/concentration as a function of voltage or current generated in the conducting or semiconducting support material. No additional components, such as supplemental reagents, are required.

Eighth, perhaps the greatest strength of this biosensor design rests in the mode of detection. Other enzyme biosensors rely on specific detectable chemistries that are associated with enzyme catalysis for detection, such as a pH change, color generation or electron transfer. This requirement significantly reduces the pool of enzymes amenable to biosensor usage in such devices. The instant biosensor, in contrast, relies on physical properties exhibited by all enzymes. Thus, any functioning enzyme should be amenable to the design. Additionally, detection on the outer surface of the sensor allows for in situ food sensing as well as the safe sensing of dangerous samples. Taken together, these developments will significantly increase the number of target molecules and products that can be subjected to biosensor analyses.

To better illustrate the invention, the following examples are provided. These examples demonstrate selected preferred embodiments of the invention and are not intended to limit the scope of the invention.

EXAMPLE 1

A piece of polyethylene (PE) is placed in an oxygen plasma or a UV-ozone cleaner. The effect is to oxidize the hydrophobic, unractive PE surface and to make it amenable to further chemical manipulations. The oxidized PE is exposed to the vapors of silicon tetrachloride ($SiCl_4$) and then water vapors. This process is repeated until the sample is shown to be fully hydrophilic ("wetted"—as measure by the contact angle value of the water on the modified PE surface). Several iterations of $SiCl_4/H_2O$ treatments may be required for preparation of PE with a chemically-bonded $SiO_2$ layer on its surface.

The modified PE sample is then exposed to the vapors of a boiling solution of ethanol, water, and the compound $(CH_3O)_3$—Si—$(CH_2)_3$—SH. This compound will create a "siloxane" network (—Si—O—Si—) between the modified surface of the PE and the compound. The PE emerging from this solution is cured in an oven. The process of subjecting the PE to the compound $(CH_3O)_3$—Si—$(CH_2)_3$—SH and heating is repeated twice again. The resultant product is a PE with a thiol (—SH) terminated SAM surface wherein the thiol groups face upwards and away from the PE.

The thiol terminated PE is placed in a commercially available electroless silvering solution and removed. A 40 nm silver (Ag) layer is thereby deposited on the PE. (Note that silver binds very tightly to the thiols on the surface of the PE). This PE/Ag is immediately placed in an ethanolic solution of compounds with the general formula HS—R—OH and 11-mercaptoundecanoic acid (11-MUA) in a 10:1 (HS—R—OH: 11-MUA) ratio. The former compound serves the following two functions:

(1) the pendant hydroxyl group (—OH) serves to hydrate the enzyme molecule on the sensor surface and provide stability to the enzyme in a nonaqueous environment because the hydroxyl group is very similar to water; and (2) the R group is chosen to balance insulation and electrical connectivity between the silver and the enzymes. R is chosen to be a phenyl group or the —$(CH_2)_6$—moiety when 11-MUA is used. The latter compound, 11-MUA, allows for enzyme immobilization.

The 11-MUA is further modified in an aqueous solution of 1-ethyl-3-[3(dimethylamino)propyl] carbodiimide hydrochloride (EDC) and N-hydroxysuccinimide (NHS). These compounds modify the 11-MUA and make it quite reactive to neutral amino ($NH_2$) groups that are present on all enzymes. The incubation is for approximately ten minutes.

The sensor is then soaked in the appropriate dilute enzyme solution at netural to slightly basic pH (one-half hour) to effect enzyme coupling to the modified PE/Ag surface through binding of lysine amino groups and the functionalized MUA. The device is removed from the enzyme solution and sonicated in an aqueous buffer to remove loosely-bound enzyme molecules. The sensor now has the following arrangement:

$PE_{(ox)}$—Si—O—Si—$(CH_3)_3$—S—Ag layer—Second Mixed SAM layer—Enzyme

Finally, the sensor is hooked up to an electrical circuit appropriate for measuring the voltage or current generated by the motion of the enzymes. Typically, the electrodes will be attached to two different positions on the silver surface.

EXAMPLE 2

A glass substrate is cleaned in an 80° C. solution of 70% sulfuric acid/30% hydrogen peroxide and then rinsed thoroughly with water. The glass is then placed in a boiling solution of ethanol, water, and the compound $(CH_3O)_3$—Si—$(CH_2)_3$—SH. This compound will create a "siloxane" network (Si—O—Si) between the glass and the compound. The glass emerging from this solution is cured in an oven. The process of subjecting the glass to the compound 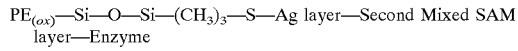 and heating is repeated twice again. The resultant product is a glass with a thiol (—SH) terminated SAM surface wherein the thiol groups face upwards and away from the glass.

The thiol terminated glass is placed in a commercially available electroless silvering solution and removed. A 40 nm silver (Ag) layer is thereby deposited on the glass. (Note that silver binds very tightly to the thiols on the surface of the glass). This glass/Ag is immediately placed in an ethanolic solution of compounds with the general formula HS—R—OH and 11-mercaptoundecanoic acid (11-MUA) in a 10:1 (HS—R—OH: 11-MUA) ratio. The former compound serves the following two functions:

(1) the pendant hydroxyl group (—OH) serves to hydrate the enzyme molecule on the sensor surface and provide stability to the enzyme in a nonaqueous environment because the hydroxy group is very similar to water; and (2) the R group is chosen to balance insulation and electrical connectivity between the silver and the enzymes. The latter compound, 11-MUA, allows for enzyme immobilization.

The 11-MUA is further modified in an aqueous solution of 1-ethyl-3-[3(dimethylamino)propyl] carbodiimide hydrochloride (EDC) and N-hydroxysuccinimide (NHS). These compounds modify the 11-MUA and make it quite reactive to amino ($NH_2$) groups that are present on all enzymes. The incubation is for ten minutes.

The sensor is then soaked in the appropriate enzyme solution to effect enzyme coupling to the modified glass/Ag surface through binding of lysine•—amino groups and the functionalized MUA. The device is removed from the enzyme solution and sonicated in an aqueous buffer to remove loosely-bound enzyme molecules. The sensor now has the following arrangement:

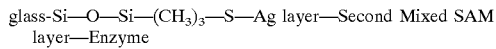
glass-Si—O—Si—(CH$_3$)$_3$—S—Ag layer—Second Mixed SAM layer—Enzyme

Finally, the sensor is hooked up to an electrical circuit as described in Example 1.

EXAMPLE 3

Example 3 is identical to example 2 except that a quartz layer is substituted for the glass layer. The sensor, prior to being hooked up to an electrical circuit as described in Example 1, has the following configuration:

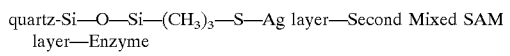
quartz-Si—O—Si—(CH$_3$)$_3$—S—Ag layer—Second Mixed SAM layer—Enzyme

EXAMPLE 4

Aluminum foil is coated with evaporated gold after an optional SAM deposition to improve the sticking of gold to the aluminum (oxide) surface. The gold is then treated as in Example 1 (from second set of SAM's and forward) to effect enzyme attachment. The functional biosensor is attached to an electrical circuit as described in Example 1.

EXAMPLE 5

A doped silicon wafer is etched with either HF or NH$_4$F to remove oxide. The resulting "reduced" silicon (SiH) is treated with a mixed SAM of HO—R—OH and HOOC—R'—COOH, in which R are R' are preferably, but not exclusively a phenyl (benzene) group. The SAM terminal carboxyl is treated with EDC and NHS, then enzyme as in Example 1, and the functional biosensor is then hooked up for detection of changes in the electrostatic potential as a function of enzyme interaction with analyte (as in Example 1).

EXAMPLE 6

The foil (no SAM or enzymes) of Example 4 is cleaned and soaked for five minutes in a dilute enzyme solution (1 microgram/milliliter). Copper leads are attached to both sides of the sensor and to a voltmeter. The sensor with physisorbed enzyme (enzyme provides insulation between electrostatic field and the gold surface) is then contacted on the gold side with the solution of interest; the presence of analyte is recorded as a function of the voltage as measured between two points on the reverse side of the sensor.

EXAMPLE 7

Silver foil is treated with 30% nitric acid and then washed well with distilled water. The foil is treated with the mixed monolayer, NHS, EDAC and enzyme sample of Example 1. Electrodes are attached to the side not in contact with the analyte. Sensing is performed by measuring the voltage difference between the electrodes when the bound enzyme is contacted with a solution that contains the analyte of interest.

EXAMPLE 8

An integrated circuit device is prepared for use as a biosensor. An enzyme is attached through an appropriate silicon-directed mixed SAM. The voltage generated by the enzymes is measured through electrodes on the device. The generated voltage is used by the device to actuate other processes. Many enzymes may be attached in unique positions on the device in order to create an enzyme "biochip".

EXAMPLE 9

Food-quality lysozyme is dissolved in doubly-distilled water (50 micrograms enzyme/milliliter water). Food-quality aluminum foil is soaked in the lysozyme solution for thirty minutes. The sensor foils are rinsed or sonicated in water to remove loosely-bound enzyme molecules. The foil (with physisorbed lysozyme) is cut into 1×1 cm$^2$ sensors. The sensor is placed into a food package so that one side faces the food, while the other side is exposed. The electrodes of a voltage meter device are contacted at two points on the exposed outer side of the sensor. Typical voltages when bacteria are present range from 3–300 millivolts. The presence of a signficant voltage indicates that bacteria are present and that the food is no longer appropriate for human consumption.

What is claimed is:

1. A biosensor for detecting the presence and/or concentration of an analyte based on the physical change in position of immobilized enzyme molecules in the presence of said analyte, comprising:
   (i) a multilayer sensor comprising a conducting or semiconducting layer and an optional self-assembled monolayer or other chemical entity directly or indirectly bound to this layer;
   (ii) enzyme molecules bound to or coordinated with the conducting or semiconducting layer of the multilayer substrate either through their interaction with the self-assembled monolayer/chemical entity or their interaction with the conducting or semiconducting support itself; and
   (iii) a means for measuring directly or indirectly electrostatic effects that result from motions of the immobilized enzyme molecules during their contact with analyte.

2. The biosensor of claim 1 wherein the self-assembled monolayer is directly and chemically bound to the conducting or semiconducting layer and wherein the enzyme molecules are directly and chemically bound to the self-assembled monolayer.

3. The biosensor of claim 1, wherein the enzyme molecules rest close enough to the conducting or semiconducting layer so as to enable changes in the location of charged portions of the enzyme molecules to generate a voltage and current in or across the conducting or semiconducting layer.

4. The biosensor of claim 1, wherein the enzyme molecules rest approximately 0–3 nanometers from the conducting or semiconducting layer.

5. The biosensor of claim 1 in which the detection of the voltage or current produced in the conducting or semiconducting material in response to enzyme motions is effected by the connection of the sensor to an appropriate voltage meter device and/or current meter device.

6. The biosensor of claim 1 in which a voltage or current meter device is connected to either the same or opposite sides of the sensor.

7. The biosensor of claim 1 wherein the multilayer substrate comprises the following layers:
   (a) a non-conducting base layer;
   (b) an optional intermediate self-assembled monolayer positioned above the base layer;

(c) an intermediate conductive layer positioned above the base layer and, if present, above the intermediate self-assembled monolayer; and (d) an outer self-assembled monolayer positioned above the intermediate conductive layer comprising one or more compounds than can bind or be made to bind with enzymes and/or provide physical stabilization to chemically bound enzymes.

8. The biosensor of claim 3 wherein the multilayer substrate comprises the following layers:

(a) a base layer containing silicon dioxide functionality chosen from the group consisting of glass, quartz, silicon, and the reaction product of an organic polymer, silicon tetrachloride and water;

(b) an optional intermediate self-assembled monolayer formed from compounds containing either an organic sulfide, disulfide or thiol group and a group that can react with silicon dioxide positioned above the base layer;

(c) an intermediate conductive layer positioned above the base layer and, if present, above the intermediate self-assembled monolayer, formed by deposition by any means of a metallic layer to the base layer;

(d) an optional outer self-assembled monolayer positioned above the intermediate conductive layer formed from one or more compounds having an organic sulfide, disulfide or thiol group and terminal functional groups that are either reactive with amino acid functionalities (or can be made reactive with said functionalities) and/or act to stabilize the enzyme molecules associated with the device.

9. The biosensor of claim 8, wherein the base layer is a reaction product of organic polymer and the vapors of silicon tetrachloride and water.

10. The biosensor of claim 8, wherein the intermediate self-assembled monolayer is formed from a compound having the formula $(CH_3O)_y$—Si—$(CH_2)_z$—SH wherein y and z, independently, may be zero or any whole integer.

11. The biosensor of claim 8, wherein the intermediate conductive layer is a silver or gold layer.

12. The biosensor of claim 8, where the outer self-assembled monolayer is formed from a mercapto acid (HS—R—COOH) and a mercapto alcohol (HS—R'—OH) wherein R and R' may be any organic groups and are chosen to balance insulation with electrical connectivity between the enzymes and the conductive layer.

13. A method for detecting and/or quantifying the presence of an analyte through the motion of enzymes in contact with said analyte comprising the following steps:

i) forming a multilayer sensor comprising a conductive or semiconductive layer and an optional self-assembled monolayer directly or indirectly bound to this layer;

ii) immobilizing enzyme molecules on the conductive or semiconductive layer of the multilayer substrate through direct or indirect binding with either the conductive/semiconductive layer or with the self-assembled monolayer; and (iii) providing a means for measuring a voltage or current generated by the movement of the enzymes in response to their contact with analyte.

14. The method of claim 13 wherein the self-assembled monolayer is directly and chemically bound to the conductive layer and wherein the enzyme molecules are directly and chemically bound to the self-assembled monolayer.

15. The method of claim 13, wherein the enzyme molecules rest close enough to the conducting or semiconducting layer to enable changes in the position of charged portions of enzyme molecules to be detected through the generation of a voltage or current in the conducting or semiconducting support material.

16. The method of claim 13, wherein the enzyme molecules rest approximately 0–3 nanometers from the conductive layer.

17. The method of claim 13 in which the leads of a voltage and/or current meter are brought into contact with the sensor on either the same or opposite sides of the sensor.

18. The biosensor of claim 1 in which the enzyme used is lysozyme and the conducting support material is aluminum foil.

19. The method of claim 13 wherein the multilayer substrate comprises the following layers:

(a) a base layer;

(b) an optional intermediate self-assembled monolayer positioned above the base layer;

(c) an intermediate conductive layer positioned above the base layer and, if present, above the intermediate self-assembled monolayer; and (d) an optional outer self-assembled monolayer positioned above the intermediate conductive layer comprising one or more compounds that chemically bind with enzymes and/or provide environmental stabilization to immobilized enzymes.

20. The method of claim 19 wherein the multilayer substrate comprises the following layers:

(a) a base layer containing an outer silicon dioxide layer chosen from the group consisting of glass, quartz, silicon, and the reaction product of an organic polymer, silicon tetrachloride and water;

(b) an optional intermediate self-assembled monolayer formed from compounds containing either a sulfide or thiol group and a group that is reactive with silicon dioxide positioned above the base layer;

(c) an intermediate conductive layer positioned above the base layer and, if present, above the intermediate self-assembled monolayer, formed by depositing a metallic solution to the base layer/SAM;

(d) an outer self-assembled (optionally mixed) monolayer positioned above the intermediate conductive layer formed from a compound having an organic sulfide, disulfide or thiol group and a terminal functional group that is reactive with amino acid functionalities (or can be made so) and a compound that has an organic sulfide, disulfide or thiol group and a terminal functional group that stabilizes enzymes through hydrophilic and/or hydrophobic interactions.

21. The method of claim 20, wherein the base layer is a reaction product of an organic polymer and the vapors of silicon tetrachloride and water.

22. The method of claim 20, wherein the intermediate self-assembled monolayer is formed from a compound having the formula $(CH_3O)_y$—Si—$(CH_2)_z$—SH wherein y and z, independently, may be zero or any whole integer.

23. The method of claim 20, wherein the intermediate conducting layer is a silver and/or gold layer.

24. The method of claim 20, where the outer self-assembled monolayer is formed from a mercapto-acid (HS—R—COOH) and a compound having the formula HS—R'—OH wherein R' may be any organic group and is chosen to balance insulation with electrical connectivity between the enzymes and the conductive layer.

25. A method for detecting and/or quantifying the presence of an analyte in a sample comprising the following steps:

(i) immobilization of enzyme molecules by any means to a solid support; and (ii) direct or indirect measurement of the changes in enzyme electrostatic fields generated by the motions of enzyme molecules during their interaction with said analyte.

26. A biosensor for detecting and/or determining the concentration of an analyte, comprising:

(i) one or more immobilized enzyme molecules; and (ii) means for measuring the voltage or current generated by the change in location of said immobilized enzyme molecules as a result of an interaction of said immobilized enzyme molecules with said analyte.

27. The biosensor of claim 26 in which the enzymes are derived from natural sources, mutagenic experiments, chemical synthesis and/or chemical modification.

28. The method of claim 25 in which the enzymes are part of an Enzyme-Linked Immunosorbent Assay (ELISA).

29. The biosensor of claim 26 in which the support material used is semiconducting in nature.

30. The biosensor of claim 26 in which the enzyme is physically absorbed directly or indirectly to a conducting or semiconducting base material.

31. The biosensor of claim 26 in which the enzyme molecule is coordinated to a self-assembled monolayer attached to a conducting/semiconducting support material.

32. The method of claim 20 in which the enzyme is bound or coordinated directly to the conducting or semiconducting support layer.

33. The biosensor of claim 26 in which the sensor is part of a solid-state electronic device.

34. The biosensor of claim 26 in which more than one enzyme is attached to a single sensor device and used in the monitoring of more than one analyte type.

35. The biosensor of claim 34 in which the device is referred to as an "enzyme chip" or an "enzyme biochip".

36. The method of claim 25 in which the energy generated by the moving enzymes is used to provide electrical energy.

* * * * *